US00PP08011P

United States Patent [19]

Olesen et al.

[11] Patent Number: Plant 8,011

[45] Date of Patent: Oct. 27, 1992

[54] MINIATURE ROSE PLANT NAMED POULWEE

[76] Inventors: Pernille Olesen; Mogens N. Olesen, both of Poulsen Roser ApS Hillerodvej 49, DK-3480 Fredensborg, Denmark

[21] Appl. No.: 642,205

[22] Filed: Jan. 16, 1991

[51] Int. Cl.[5] ..... A01H 5/00

[52] U.S. Cl. ..... Plt./8.2

[58] Field of Search ..... Plt. 8

*Primary Examiner*—Howard J. Locker

[57] ABSTRACT

A new and distinct variety of miniature rose plant particularly distinguished by its profuse production of small, Lemon Yellow flowers growing on a small, compact, upright bush having a height of about 17 cm. at six weeks of growth with a main stem length of 10 to 12 cm. from the last flower cut and a vigorous, free branching growth habit with small but abundant foliage.

1 Drawing Sheet

BACKGROUND OF THE NEW PLANT

This plant originated as a hybrid seedling developed by us at Kvistgaard, Denmark by crossing an unnamed seedling selected from our collection at our Denmark nursery with pollen from the variety 'Texas', U.S. Plant Pat. No. 6,261 with the object of developing a Yellow long lasting miniature rose which does not fade in color. The present seedling derived from the said hybrid was selected for propagation because of its profuse production of relatively small flowers carried singly on strong, straight stems growing in a raceme manner from a main stem of a plant having a total height of about 17 cm. The flower color of Lemon Yellow with a diameter of 3½ to 4 cm. appeared to meet our objectives and accordingly this selected seedling was asexually reproduced by us at our Denmark nursery both by means of cuttings as well as budding on stock with such pleasing results that such propagation was continued through several successive generations which demonstrated conclusively that the novel characteristics of the original selected seedling were carried on from generation to generation and appeared to be firmly fixed. At present, propagation is carried on by means of cuttings in pots for pot forcing and this is done in Denmark as well as in Japan.

DESCRIPTION OF THE DRAWING

Our miniature rose plant is illustrated by the accompanying full color photographic drawings which show face views of a pair of fully opened flowers together with views of the upper side and the under side of a typical leaf of the new plant, the colors shown being as nearly true to those herein specified as is possible to obtain by conventional photographic procedures.

DESCRIPTION OF THE NEW VARIETY

The following is a detailed description of our new miniature rose plant as observed from plants grown at our nursery greenhouse with color designations being according to The R.H.S. Colour Chart published by The Royal Horticultural Society of London, England.

THE PLANT

Origin: Seedling.

Parentage:

*Seed parent.*—An unnamed seedling selected from our rose collection at our Denmark nursery.

*Pollen parent.*—The variety 'Texas' (U.S. Plant Pat. No. 6,261).

Classification:

*Botanic.*—Rosa Hybrid Miniature Rose.

*Commercial.*—Miniature Rose Pot Plant.

Form: Herbaceous bush.

Shape: Small, compact and upright.

Height: At six weeks, 17 cm.

Growth rate: Vigorous.

Main Stem:

*Length.*—10 to 12 cm. from last flower cut.

*Color.*—Yellow Green 146-A.

Branching character: Free branching.

Strength: Very sturdy for a mini-flora.

Foliage:

*Quantity.*—Abundant.

*Number of Leaves.*—6 or 7 from last flower cut.

*Leaf type.*—Odd pinnate.

*Size.*—About 5½ to 6 cm. in length.

*Leaflets.*—Number: 3 or 5, usually 5. Shape: Oval with denticulate margins. Size: About 20 mm.×15 mm. Texture: Semi-leathery. Aspect: Smooth and glossy. Color: Upper side — Yellow Green 147-A. Under side — Yellow Green 147-B. Stipules: Adnate, tipped with glands. Rachis: Length: About 40 to 45 mm. on 3 part leaf; and 55 to 60 mm. on 5 part leaf. Petioles: Length: About 6 to 7 mm. on 3 part leaf; and 9 to 11 mm. on 5 part leaf.

Ribs and veins: Slightly depressed on top side and rounded on the other side.

Thorns: None.

THE BUDS

Size: Small.

*Diameter.*—About 13 mm.

*Length.*—About 14 mm.

Shape: Globular and slightly pointed.

Rate of opening: Moderate.

Color of petals:

*When sepals first divide.*—Yellow orange 14-B.

*When petals begin to unfurl.*—Yellow 12-A.

Sepals:

*Number.*—5.

*Shape.*—Spreading, some with leaf pointed ends and leafs protruding from the sides.

*Character.*—Hooded over the bud and standing up when flowers open.

*Color.*—Inside color — Green 138-B and covered with Whiteish hairs. Outside color — Yellow Green 146-B.

Calyx:

*shape.*—Pear-shaped.

*Size.*—Small, about 5 mm. wide and about 5 to 7½ mm. long.

*Splitting.*—The calyx does not split.

*Aspect.*—Smooth.

Peduncle of flower stem:

*Length: About* 35 to 45 mm. with no hairs.

*Character: Slender and erect.*

Color: Yellow Green 144-A.

THE FLOWER

Blooming habit: Continuous and profusely from early Spring to late Fall, blooming freely in Fall.

Size of bloom: Small.

*Diameter.*—About 35 to 40 mm. when fully opened.

*Depth.*—10 mm.

Borne: Singly on strong, upright stems.

Shape:

*When bloom first opens.*—Cup shaped.

*When bloom matures.*—The petals reflex slightly.

Petalage:

*Number.*—26 to 28.

*Arrangement.*—Nicely imbricated.

*Form.*—Spoon shaped with acute apex and margins that slightly curl under.

*Texture.*—Soft.

*Aspect.*—Velvety.

*Color.*—Outer petals: Body and Base - Aureolin 12-A. Reverse side: 13-B. Inside petals: Body and Base - Yellow Orange 14-B. Reverse side: Yellow 13-A.

*Petaloids.*—Number: 1 or 2. Size: About 7 mm.

Discoloration after full bloom: None.

Effect of weather: Very little growing in greenhouse.

Persistence: The flower will dry and then the petals will fall.

Disease resistance: Moderately resistant to mildew, rust and black spots as observed at Watsonville, Calif.

Fragrance: Rather slight.

Lasting quality: Long lasting on plant, not used as cut flower.

THE REPRODUCTIVE ORGANS

Stamens:

*Number.*—About 41.

*Arrangement.*—Introrse.

*Anthers.*—Size: About 3 mm. Color: Yellow Orange 21-B.

*Filaments.*—Length: 4 or 5 mm. Color: Yellow Orange 21-C.

*Pollen.*—Color: Yellow Orange 20-B.

Pistils:

*Number.*—About 23.

*Styles.*—Length: About 6 or 7 mm. Color: Yellow 2-D.

*Stigmas.*—Color: Chartreuse Green.

Character of the ovaries: Small, rounded and covered with silvery hairs.

THE FRUIT

Fertility: The fruit is fertile.

Shape: Round.

Color: Greyed Red 163-B.

We claim:

1. The new and distinct miniature pot rose plant, substantially as herein shown and described, characterized by its profuse production of small Yellow Orange colored flowers having a diameter of about 4 cm. or less borne on a small, compact bush having a height of about 18 cm. and a vigorous, compact, upright growth habit.

* * * * *

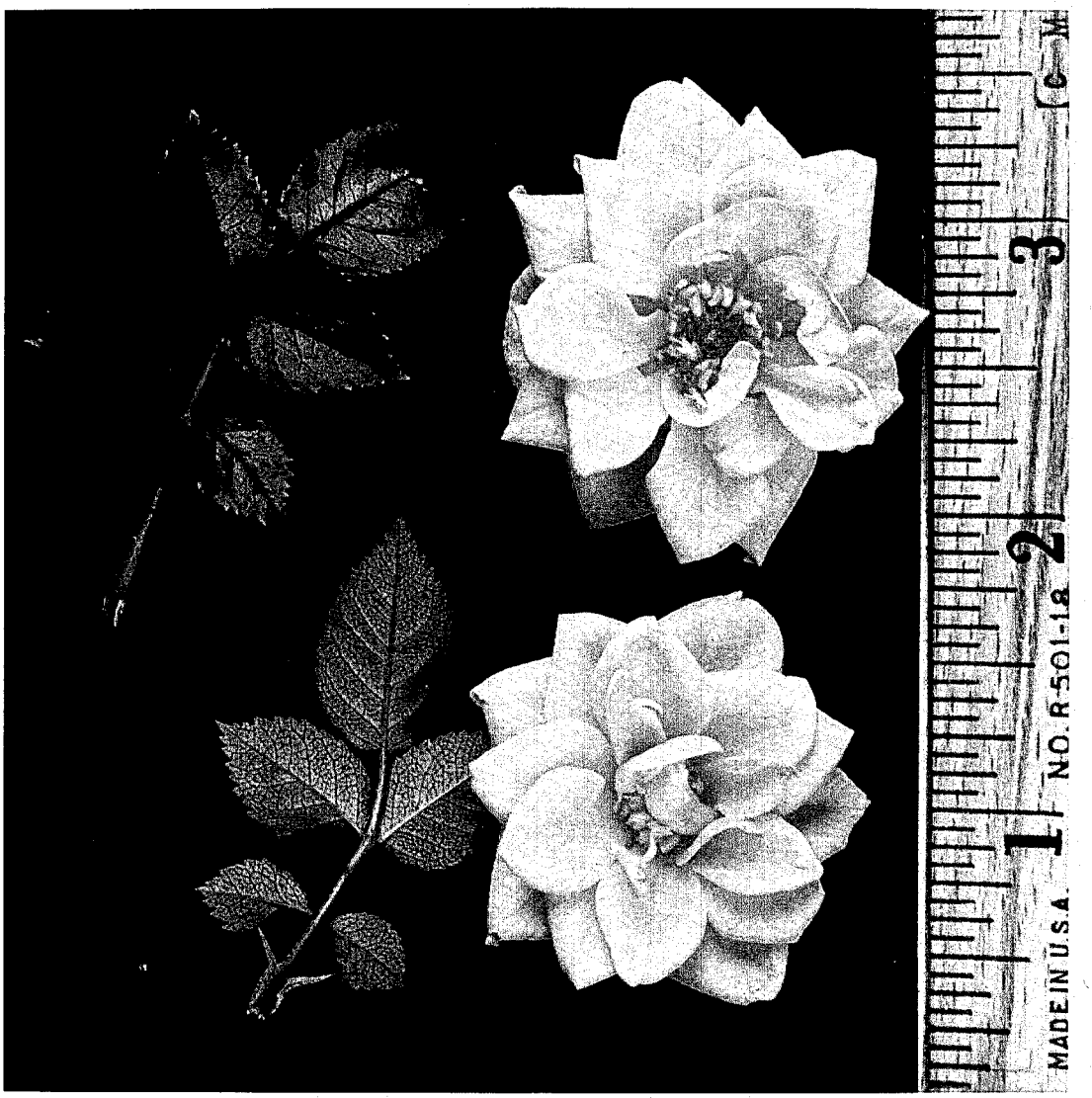
MADE IN U.S.A.
NO. R-501-12
1
2
3
CM

UNITED STATES PATENT AND TRADEMARK OFFICE

CERTIFICATE OF CORRECTION

PATENT NO. : Plant 8,011

DATED : Oct. 27, 1992

INVENTOR(S) : Olesen et al.

It is certified that error appears in the above-identified patent and that said Letters Patent is hereby corrected as shown below:

On title page, add, item [73]
Assignee: DeVor Nurseries, Inc., Freedom, Calif.

Signed and Sealed this

Fifth Day of October, 1993

*Attest:*

*Attesting Officer*

BRUCE LEHMAN

*Commissioner of Patents and Trademarks*